(12) United States Patent
Bles et al.

(10) Patent No.: US 6,613,003 B1
(45) Date of Patent: Sep. 2, 2003

(54) TEST APPARATUS FOR DETERMINING A CERVICAL ACCELERATION INJURY

(75) Inventors: Willem Bles, Soest (NL); Joachim Lok, Amsterdam (NL); Jean Marie Baptiste Vianney De Jong, Amsterdam (NL)

(73) Assignee: Hollandse Exploitatie Maatschappij B.V., Amsterdam (NL)

( * ) Notice: Subject to any disclaimer, the term of this patent is extended or adjusted under 35 U.S.C. 154(b) by 0 days.

(21) Appl. No.: 09/743,727

(22) PCT Filed: Jul. 14, 1999

(86) PCT No.: PCT/NL99/00450

§ 371 (c)(1),
(2), (4) Date: Apr. 24, 2001

(87) PCT Pub. No.: WO00/03638

PCT Pub. Date: Jan. 27, 2000

(30) Foreign Application Priority Data

Jul. 14, 1998 (NL) .............................................. 1009646

(51) Int. Cl.[7] .......................... A61B 5/103; A61B 5/117
(52) U.S. Cl. ...................................... 600/595; 600/587
(58) Field of Search ................................. 600/595, 546, 600/587, 559; A61B 5/00, 5/10, 5/11

(56) References Cited

FOREIGN PATENT DOCUMENTS

| WO | 8804909 | 7/1988 | ............ A61B/5/00 |
| WO | 8805285 | 7/1988 | ............ A61B/5/10 |
| WO | 9115148 | 10/1991 | |

OTHER PUBLICATIONS

W. Bles et al.; The tilting room and posturography; 1991; pp. 387–391.
K. Taguchi; Concentrically Moving Multi–Spotlights Stimulation; 1986; pp. 1594–1595.
B. E. Maki et al.; A Posture Control Model and Balance Test for the Prediction of Relative Postural Stability; 1987; pp. 797–810.

*Primary Examiner*—Henry Bennett
*Assistant Examiner*—Sabrina Dagostino
(74) *Attorney, Agent, or Firm*—Webb Ziesenheim Logsdon Orkin & Hanson, P.C.

(57) ABSTRACT

Device for performing a test supplementary to neurological examination, which determines whether a cervical acceleration injury has occurred, which device comprises a platform connected non-movably to a fixed ground for supporting a person, a visually manipulable environment in which the person is placed, in addition to sensors connected to the platform and/or to the person for measuring postural corrections of the person, and computing means connected to the sensors, wherein means are arranged for comparing the values generated by the sensors with standard values in order to obtain a measure for the visual dependency of the person; and a method of determining a cervical acceleration injury. With the invention measurements can be performed in objective manner with which an objective judgment in respect of the presence of a cervical acceleration injury in the person in question can be obtained.

9 Claims, 3 Drawing Sheets

TEST APPARATUS FOR DETERMINING A CERVICAL ACCELERATION INJURY

BACKGROUND OF THE INVENTION

1. Field of the Invention

The present invention relates to a device for performing a test supplementary to neurological examination, which determines whether a cervical acceleration injury has occurred. In addition, the invention relates to a method of determining a cervical acceleration injury.

2. Background Art

A cervical acceleration injury, also known as whiplash, manifests itself in persons who have been run into from behind in a vehicle. It has been proven statistically that a combination of symptoms of a subjective character, such as headache, loss of concentration, memory loss and fatigue, is related to being run into from behind. However, medical researchers have to date been unable to find any anatomical substrate or pathophysiological mechanism which explains this combination of symptoms. Insurance companies and benefits agencies are dependent on the subjective judgment of a medical practitioner, who determines whether the person has a cervical acceleration injury.

SUMMARY OF THE INVENTION

The present invention has for its object to provide a possibility of determining in objective manner whether a cervical acceleration injury has occurred. For this purpose a device is provided for performing a vestibular test supplementary to a neurological examination. The device of the present invention comprises a platform connected non-movably to a fixed ground for supporting a person, a visually manipulable environment in which the person is placed, in addition to sensors connected to the platform and/or to this person for measuring postural corrections of this person, and computing means connected to the sensors, wherein means are arranged for comparing the values generated by the sensors with standard values in order to obtain a measure for the visual dependency of this person.

Measurements are hereby performed in objective manner with which an objective judgment in respect to the presence of a cervical acceleration injury in the person in question can be obtained. The judgment is based on objective changes in the postural balance as observed in a large group of people with an identical pattern of symptoms which manifests itself following a cervical acceleration injury.

The visually manipulable environment is preferably formed by a tilting room. The person is situated on the platform arranged in the tilting room, whereby he is subject to a visually manipulable environment.

What is in effect measured in the device is how the postural balance of a person functions under different conditions of the body of the person and of the environment, for instance the tilting room, in which the person is standing. In order to be able to cause the person to react realistically to his environment, the person will have to have the most realistic possible idea of the environment in which he is situated. For this purpose the room tilts on imaginary lines running through or close to the centre of the platform.

In order to be able to draw conclusions in simple manner from the performed examination, the comparing means are part of the computing means.

BRIEF DESCRIPTION OF THE DRAWINGS

The present invention will be further elucidated with reference to the description following hereinbelow and the annexed drawings. In the drawings.

DETAILED DESCRIPTION OF THE PREFERRED EMBODIMENT

Figure 1:
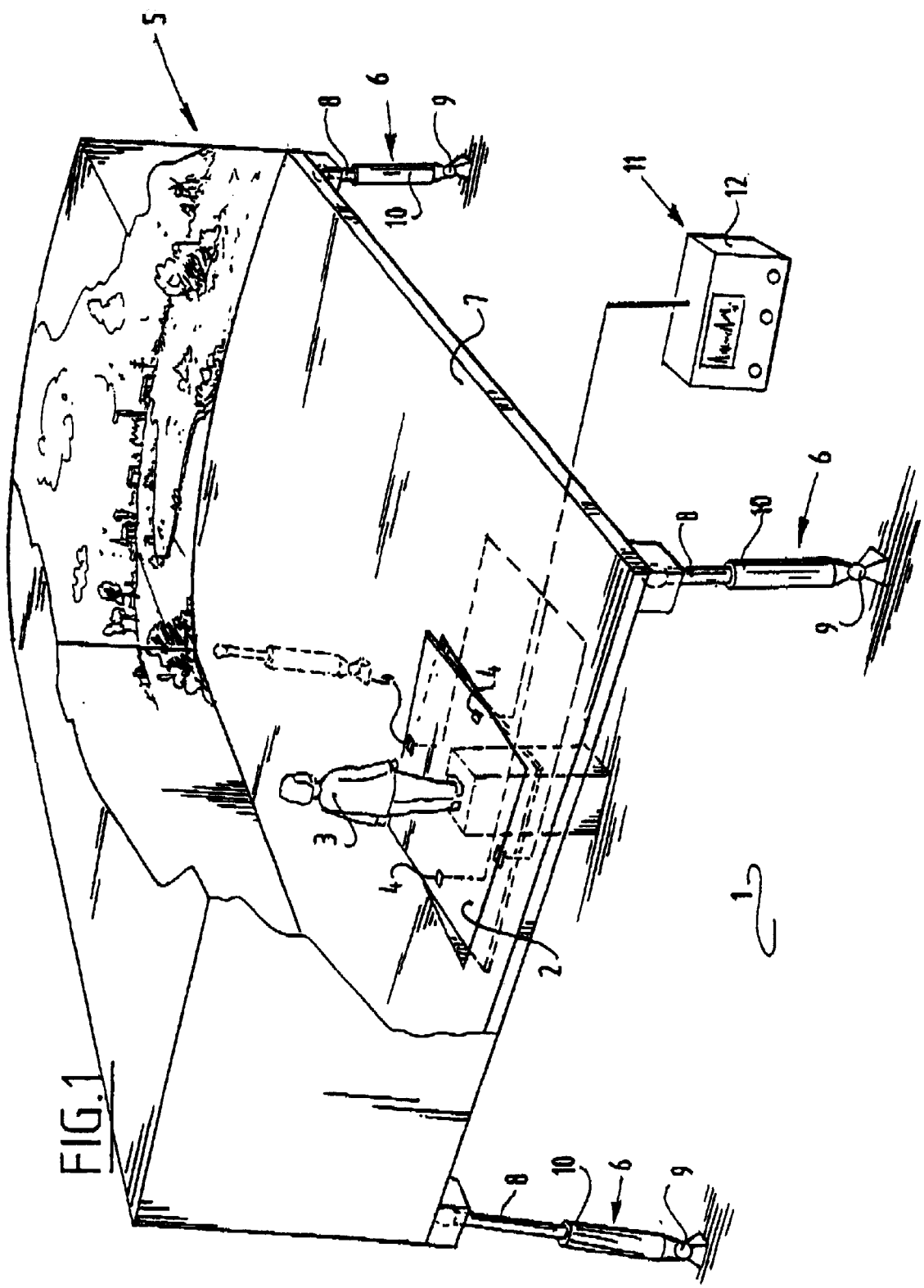
FIG. 1 shows an embodiment of the device according to the invention.

FIG. 1 shows an embodiment of a device according to the invention for performing a test supplementary to the neurological examination, which test determines whether postural changes as stated above have occurred.

The device comprises a platform 2 connected non-movably to a fixed ground 1 for supporting a person 3. Force sensors 4 for measuring the weight displacement of person 3 are connected to platform 2. Platform 2 is accommodated in a tilting room 5 which can be tilted in different directions relative to fixed ground 1 by means of displacing means 6.

Displacing means 6 can be formed by cylinders 8 which are connected to the bottom 7 of tilting room 5 and which are received slidably in cylinders 10 connected to fixed ground 1 by means of ball joints 9. Displacing means 6 are operated individually to cause tilting room 5 to tilt in miscellaneous directions relative to fixed ground 1. Tilting room 5 will in any case tilt around imaginary lines running through or close to the centre of platform 2.

Force sensors 4 are coupled to computing means 11. Comparing means 12 are likewise arranged in computing means 11 to enable comparison of the values generated by force sensors 4 with standard values in order to obtain a measure for the visual dependency of person 3.

The test, which determines whether a cervical acceleration injury has occurred, is carried out on persons 3, wherein injury other than a possible cervical acceleration injury has been precluded by the neurological examination. The test includes a stabilometric examination and a tilting room examination.

In the stabilometric examination the weight displacement of person 3 is measured by the force sensors 4 on platform 2 under different conditions of the body of this person 3, for instance with eyes open and eyes closed, head upright and head tilted back. The values generated by force sensors 4 are entered into computing means 11.

In the tilting room examination the person 3 stands with his eyes open and his head upright on platform 2, wherein tilting room 5 is tilted in determined directions. The weight displacement of this person 3 is again measured by force sensors 4 on platform 2 and transmitted to computing means 11.

All values generated by force sensors 4 in the stabilometric examination and tilting room examination are compared with standard values using comparing means 12 in order to obtain a measure for the visual dependency of this person 3. The standard values are obtained by subjecting a healthy group of people with a normally functioning postural balance to the same examination. When the postural balance of the examined person differs from that of the healthy group of people, it is possible, if the correct criteria are applied, to determine whether this person has a cervical acceleration injury.

EXAMPLE

The test included a stabilometric examination and a tilting room examination (for description see: "The tilting room and posturography" Acta oto-rhino-laryngo-logica belg. 1991. 45, 387–391) and was carried out on patients, wherein injury other than a possible cervical acceleration injury had been precluded by a neurological examination. Three groups of people underwent such a test, two groups of people suffering from a "whiplash"-syndrome (patient group, PG) and one group of healthy people (control group, CG).

During the stabilometric examination the forward-backward (VA) and the sideward (LR) postural corrections are measured in three measuring conditions, i.e. "standing with eyes open" (OO), "standing with eyes closed" (OD) and "standing with eyes closed, head tilted back" (HNA). For each measuring condition the root mean squares (RMS) are determined of both the VA and the LR stabilogram.

The RMS of stabilogram is a measure for the stability of the postural balance. The determined RMS values of stabilogram are plotted for the three groups and for the three measuring conditions in the graph of FIG. 1.

During the tilting room examination the VA and LR postural corrections are measured in two measuring conditions. In the first measuring condition (KK1) the tilting room is moved at a frequency of 0.025 Hz and an amplitude of 5°. In the second measuring condition (KK4) the frequency of the movement of the tilting room was 0.2 Hz and the amplitude thereof was likewise 5°. The measurement results are plotted in the graph of FIG. 3.

Figure 2:
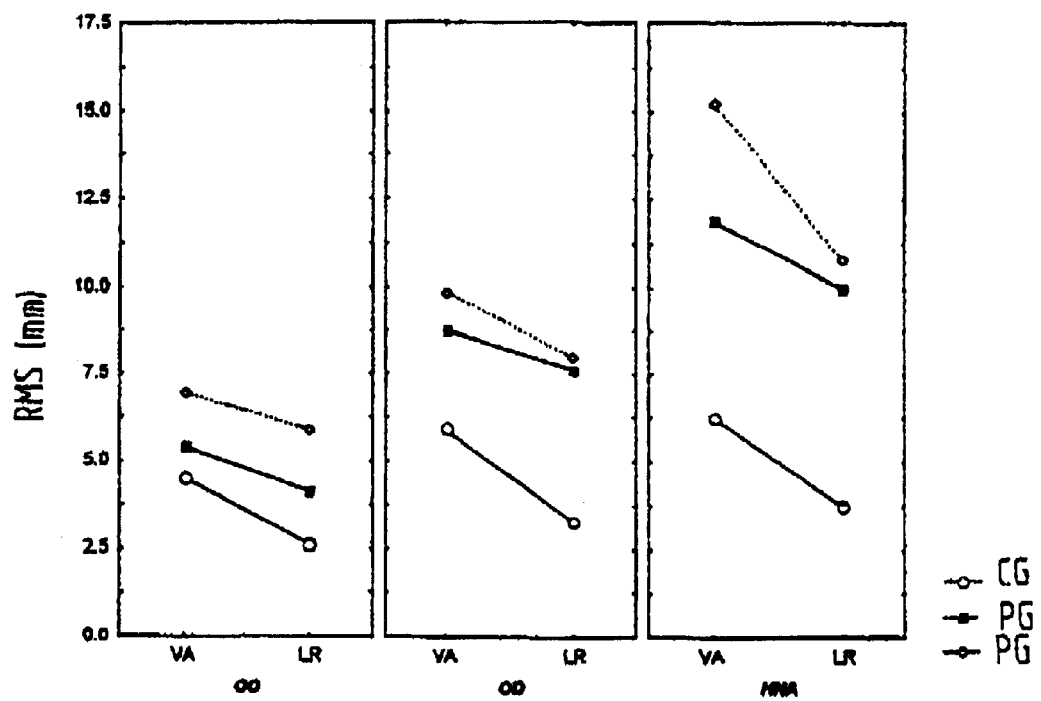
FIG. 2 shows a graph with measurement results from a stabilometric examination.
Figure 3:
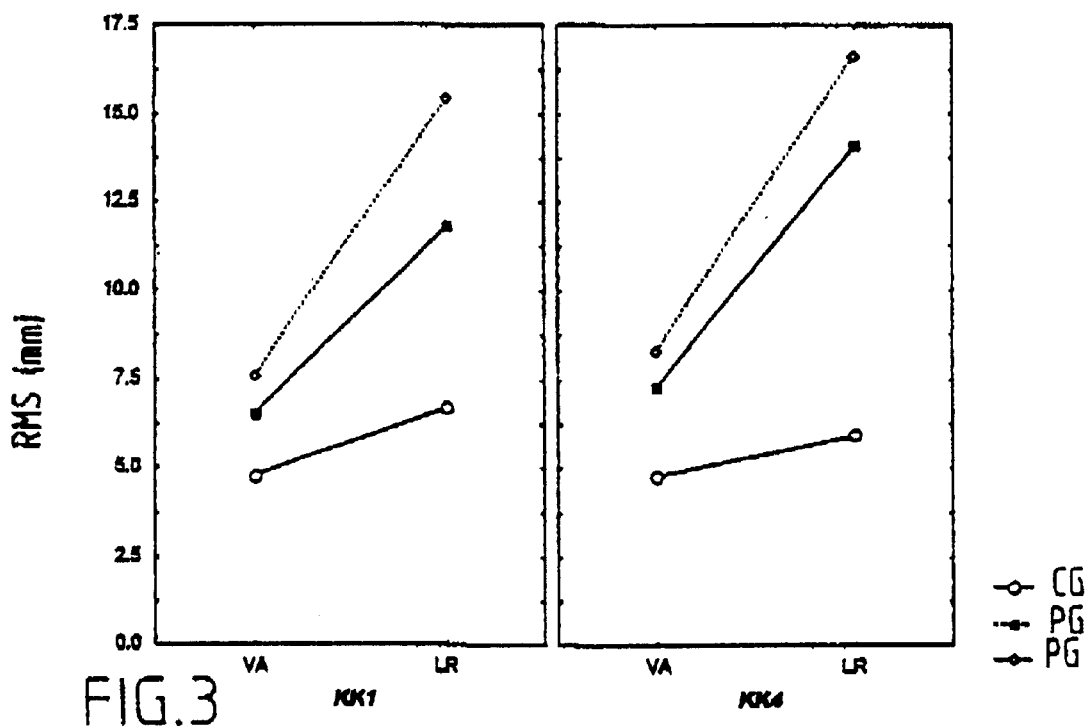
FIG. 3 shows a graph with measurement results from a tilting room examination.

From the graphs of FIGS. 2 and 3 it can be established that in a number of the examined conditions the postural balance in the 2 patient groups (PG) clearly differs from that of the control group (CG).

Figure 4:
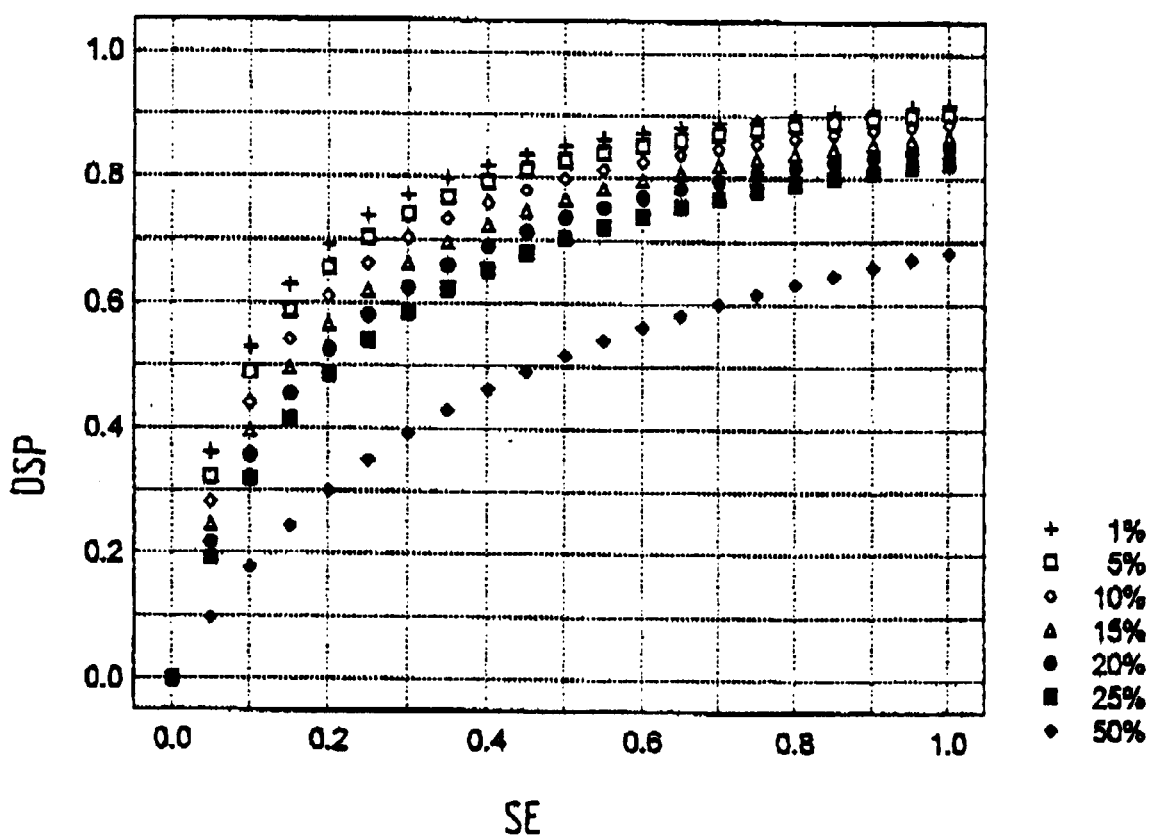
FIG. 4 shows a graph in which the diagnostic specificity is plotted out against the sensitivity for different percentages of fraudsters and for which data from both examinations is used.

It has been found that, if in a fully performed stabilometric and tilting room examination the RMS-value of the VA-stabilogram during the condition "eyes closed, head tilted back" is greater than 9 mm, and the RMS-value of the LR-stabilogram in the tilting room stimulation at 0.2 Hz is greater than 8.5 mm, a cervical acceleration injury can then be established with 90% certainty. If a person meets these two criteria, this is referred to as a positive test. In the graph of FIG. 4 the diagnostic specificity (the chance illness is present when a test is positive, DSP) is plotted as a function of the sensitivity (chance of positive test when illness is present, SE) at different percentages of fraudsters. This shows that with the two criteria HNA VA>9 and KK4_ LR>8.5 it is possible to state with a certainty of 90% that a person has a cervical acceleration injury if his test is positive.

Although the conditions HNA and KK4 provide the clearest differences, it is recommended to carry out the whole examination (thus including other head/eye-conditions and tilting room frequencies), since the total examination result must provide a consistent picture.

The invention is not limited to the above described device. It is thus possible for instance to use resistance strain gauges instead of force sensors to detect weight displacement, or pressure changes of the feet on the platform, of the person. In addition, the sensors can be arranged on the person himself. It is also possible to use virtual reality instead of a tilting room to obtain a visually manipulable environment in which the person is placed.

What is claimed is:

1. A device for performing a vestibular test comprising:
    a platform connected non-movably to a fixed ground for supporting a person,
    a visually manipulable environment in which the person is placed,
    sensors connected to the platform and/or the person for measuring postural corrections of the person,
    computing means connected to the sensors, and
    comparing means for comparing the values generated by the sensors with standard values, wherein determining means for applying predetermined criteria when the measured values differ from the standard values to determine whether the person has a cervical acceleration injury.

2. The device according to claim 1, wherein the computing means computes the root mean square (RMS) of at least the forward-backward (VA) and sideward (LR) postural corrections.

3. The device according to claim 2, wherein the visually manipulable environment is formed by a tilting room.

4. The device according to claim 3, wherein the room tilts on imaginary lines running through or close to the centre of the platform.

5. The device according to claim 3, wherein the criteria are defined as follows:
    the RMS-value of the VA postural corrections during the condition "eyes closed, head tilted back" is greater than 9 mm (HNA_VA>9), and
    the RMS-value of the LR postural corrections in the tilting room stimulation at 0.2 Hz is greater than 8.5 mm (KK4_LR>8.5).

6. A method of determining a cervical acceleration injury, comprising:
    performing a neurological examination,
    supporting a person on a platform connected non-movably to a fixed ground,
    arranging sensors on the person and/or the platform,
    measuring postural corrections of the person under different conditions of his body using these sensors,
    placing the person in a visually manipulable environment,
    measuring postural corrections of the person using these sensors under different conditions of the environment in which he is located,
    comparing the values generated by the sensors with standard values,
    applying predetermined criteria when the measured values differ from the standard values to determine whether the person has a cervical acceleration injury.

7. The method according to claim 6, wherein the root mean square (RMS) of at least the forward-backward (VA) and sideward (LR) postural corrections is computed prior to comparing the values.

8. The method according to claim 7, wherein a tilting room is chosen for the visually manipulable environment.

9. The method according to claim 2, wherein the criteria are defined as follows:
    the RMS-value of the VA postural corrections during the condition "eyes closed, head tilted back" is greater than 9 mm (HNA_VA>9), and
    the RMS-value of the LR postural corrections in the tilting room stimulation at 0.2 Hz is greater than 8.5 mm (KK4_LR>8.5).

* * * * *

UNITED STATES PATENT AND TRADEMARK OFFICE
CERTIFICATE OF CORRECTION

PATENT NO. : 6,613,003 B1  Page 1 of 1
DATED : September 2, 2003
INVENTOR(S) : Willem Bles et al.

It is certified that error appears in the above-identified patent and that said Letters Patent is hereby corrected as shown below:

Column 3,
Line 50, "HNA VA", should read -- HNA_VA --.
Lines 50-51, "KK4 LR", should read -- KK4_LR --.

Column 4,
Line 58, "2" should read -- 8 --.

Signed and Sealed this

First Day of June, 2004

JON W. DUDAS
*Acting Director of the United States Patent and Trademark Office*